(12) United States Patent
Settlage et al.

(10) Patent No.: US 6,315,905 B1
(45) Date of Patent: Nov. 13, 2001

(54) METHOD FOR STRUCTURAL CHARACTERIZATION OF BIOLOGICAL MOIETIES THROUGH HPLC SEPARATION

(75) Inventors: Robert E. Settlage; Donald F. Hunt; Robert E. Christian, all of Charlottesville, VA (US)

(73) Assignee: University of Virginia Patent Foundation

( * ) Notice: Subject to any disclaimer, the term of this patent is extended or adjusted under 35 U.S.C. 154(b) by 0 days.

(21) Appl. No.: 09/489,618

(22) Filed: Jan. 24, 2000

Related U.S. Application Data (62) Division of application No. 09/175,477, filed on Oct. 20, 1998, now Pat. No. 6,139,734.
(60) Provisional application No. 60/062,486, filed on Oct. 20, 1997.

(51) Int. Cl.[7] .................................................. B01D 15/08
(52) U.S. Cl. ...................... 210/656; 210/659; 210/198.2; 250/288
(58) Field of Search ...................... 210/635, 656, 210/659, 748, 198.2, 243; 250/288; 422/70; 436/161

(56) References Cited

U.S. PATENT DOCUMENTS

| | | | |
|---|---|---|---|
| 4,654,052 | * 3/1987 | Sharp | 210/198.2 |
| 5,015,845 | * 5/1991 | Allen | 250/288 |
| 5,037,611 | * 8/1991 | Ledford | 250/288 |
| 5,237,175 | * 8/1993 | Wells | 250/288 |
| 5,346,622 | * 9/1994 | Klee | 210/659 |
| 5,491,096 | * 2/1996 | Sportsman | 210/198.2 |
| 5,495,108 | * 2/1996 | Apffel | 250/288 |
| 5,750,988 | * 5/1998 | Apffel | 250/288 |
| 5,872,010 | * 2/1999 | Karger | 210/198.2 |

OTHER PUBLICATIONS

Hunt, Donald F., et al., "Mass Spectrometric Methods for Protein and Peptide Sequence Analysis," Techniques in Protein Chemistry II, Academic Press, Inc., p. 441–454, (May 30, 1991).

Davis, M.T., et al., "Low Flow High–Performance Liquid Chromatography Solvent Delivery System Designed for Tandem Capillary Liquid Chromatography–Mass Spectrometry," Journal American Society for Mass Spectrometry, p. 571–577, (May 30, 1995).

(List continued on next page.)

Primary Examiner—Ernest G. Therkorn
(74) Attorney, Agent, or Firm—Robert J. Decker (57) ABSTRACT

A system allows routine coupling of HPLC separations to sheathless $\mu$-ESI sources for MS analysis. Characteristics of this system include stable electrospray throughout the HPLC gradient at low and high flow rates, lower background than conventional sources, and control over the width of eluting HPLC peaks without degradation of HPLC performance. This system includes a pre-column solvent flow splitter, a metal union in the split waste line for application of $\mu$-ESI voltage, a divert valve containing two different size restrictors for control of flow, and pulled fused silica capillaries as $\mu$-ESI emitters. The pulled tips allowed stable operation of the system with column flow rates ranging from ca. 5→250 nL/min.

5 Claims, 7 Drawing Sheets

OTHER PUBLICATIONS

Davis, Michael T., et al., "A Microscale Electrospray Interface for On–Line, Capillary Liquid Chromatography/Tandem Mass Spectrometry of Complex Peptide Mixtures," Analytical Chemisry, American Chemical Society, vol. 67 (No. 24), p. 4549–4556, (May 30, 1995).

Wilm, Matthias S., et al., "Electrospray and Taylor–Cone theory, Dole's beam of macromolecules at last?," International Journal of Mass Spectrometry and Ion Processes, Elsevier Science B.V. (Amsterdam, Netherlands), p. 167–180, (May 30, 1994).

Cox, Andrea L., "Identification of a Peptide Recognized by Five Melanoma–Specific Human Cytotoxic T Cell Lines," Science, p. 716–719, (Apr. 29, 1994).

Kriger, M. Scott, et al., "Durable Gold–Coated Fused Silica Cepillaries for Use in Electrospray Mass Spectrometry," Analytic Chemistry, American Chemical Society, vol. 67 (No. 2), p. 385–389, (Jan. 15, 1995).

Wilm, Matthias, "Analytical Properties of the Nanoelectrospray Ion Source," Analytical Chemistry, American Chemical Society, vol. 68 (No. 1), p. 1–8, (Jan. 1, 1996).

Wahl, Jon H., et al., "Sheathless capillary electrophoresis–electrospray ionization mass spectropetry using 10 micrometer I.D. capillaries: analyses of tryptic digests of cytochome c," Journal of Chromatography, Elsevier Science B.V. (Amsterdam, Netherlands), p. 217–222, (May 30, 1994).

\* cited by examiner

METHOD FOR STRUCTURAL CHARACTERIZATION OF BIOLOGICAL MOIETIES THROUGH HPLC SEPARATION

This application is a regular National application claiming priority from U.S. patent application Ser. No. 09/175,477, filed Oct. 20, 1998, now U.S. Pat. No. 6,139,734, and Provisional Application, U.S. application Ser. No. 60/062,486 filed Oct. 20, 1997. The entire disclosure of the the aforesaid are incorporated herein by reference.

BACKGROUND OF THE INVENTION

1. Field of the Invention

This invention pertains to an apparatus and method for characterizing peptides and other biological moieties by electrospray ionization mass spectrometry of samples provided by high performance liquid chromatography (HPLC). A device is provided which permits broadening of HPLC elution peaks without loss of resolution, simultaneously slowing the solvent flow of the system without burdening the system with substantial dead volume for the HPLC eluent. The device also provides for application of the voltage necessary for sheathless electrospray ionization in a waste line thereby overcoming issues related to application of the voltage.

2. Background of the Prior Art

Mass spectrometry has rapidly developed as the method of choice for sequencing biologically derived molecules.[1,2] The high complexity of biological mixtures often makes coupling a separation technique, such as HPLC, highly desirable or even required.[2] Unfortunately, for many detection techniques including mass spectrometry, as the separation efficiencies increase, the peak widths tend to narrow placing more stringent speed requirements on the mass spectrometer (MS), making structural analysis of peptides by collisionally-activated dissociation (CAD) difficult.

Also important in many biological analysis is the detection limit of electrospray ionization MS techniques. Electrospray ionization (ESI) efficiencies with conventional ESI sources are compromised in two ways. First, as an analyte enters into the ionization region of the ESI source it is diluted by a sheath liquid to help stabilize the ESI process and apply the potential needed for ESI to the HPLC effluent.[3] Second, the large electrospray plume generated by the convention ESI source is sampled by a very small orifice leading into the MS giving low transmission efficiencies.[4] Recent advances in ESI techniques have shown improvements in ESI transmission efficiencies by eliminating sheath liquids and reducing total flows into the ESI source.[3-8]

One of the most widely used miniaturized sheathless ESI sources ($\mu$-ESI) is the Nanospray source of Mann et al.[5] This source uses glass capillaries pulled to <5 $\mu$m, sample flow rates at <5–50 nL/min, and is capable of analyzing low femtomole amounts of sample in a volume of 1 $\mu$L continuously for more than 1 hour. The long analysis time allows multiple MS experiments to be performed. This method, however, often requires substantial signal averaging (>10 min) to acquire satisfactory S/N to identify precursor masses for subsequent CAD experiments and does not have the ability to interface with a separation technique. The tips for this source are fragile, expensive, non-reusable, and the position of the tip at the orifice into the mass spectrometer is critical, often requiring expensive camera equipment in order to achieve optimum signal.

The use of reverse phase HPLC on line with $\mu$-ESI for the analysis of peptide mixtures offers numerous advantages over Nanospray ESI, including desalting and detergent removal, complicated mixtures can be time resolved, more dilute samples can be used because the sample is concentrated on column, and information on the hydrophobicity of the analyte can be obtained. However the short time window in which a peptide elutes can be problematic if multiple stages of MS are desired. In order to sequence biological peptides using MS, it is necessary to 1) identify the peptide and 2) dissociate the peptide such that it fragments randomly along the amide linkages. CAD on the ion trap MS involves several steps. The precursor ion must first be isolated using tailored rf waveforms applied to the endcap electrodes. The ion must then be activated by increasing the ions kinetic energy using rf waveforms applied to the endcaps in resonance with the ion in the, presence of a bath gas such that the ion collides with the bath gas converting kinetic energy into internal energy. The ion then may fragment and the fragments are scanned out and detected. This identification/CAD process can be 5 seconds while typical HPLC peak widths are ca. 12 seconds.

It has been shown that slowing the flow rate down during an HPLC run can satisfactorily increase the elution time of a peptide by as much as 10 times.[7,8] Potential problems with this method for commercial syringe pump HPLC systems are the time delay before the slow column flow is realized and the dead volume of the system after slow column flow is achieved. The time delay before slow column flow is achieved arises from the total volume of the system being at the running pressure of the column. To slow down the column flow the entire HPLC system pressure must be reduced to the desired low column flow pressure. The second potential problem is the dead volume after the solvent mixing tee. The desired HPLC gradient must pass through the dead volume after the mixing tee at the slow flow rates, this will give significant lag times in the HPLC gradient profiles. Davis et al. use a preformed gradient in a fused silica capillary (FSC) and a programmable ISCO syringe pump to slow down and speed up the flow rate of the mobile phase over the column.[7] To combat the lag time before slow flow is achieved they actually reverse the syringe pump to lower the column head pressure very quickly. The preformed gradient fixes the profile of the HPLC run before changing pressures such that they have no HPLC gradient lag times due to dead volumes. Unfortunately, these methods to overcome dead volume issues will not work with more common HPLC syringe pump systems.

Accordingly it remains an object of those of skill in the art to develop a process to characterize biological molecules and compounds by MS, particularly, through ESI MS. It is a further object of those of skill in the art to provide an apparatus that permits broadening of HPLC peaks in an ESI environment, without dead volume and at a slow or controlled flow rate.

SUMMARY OF THE INVENTION

The above objects, and others described in more detail below, are met by providing an apparatus comprising an HPLC column joined with an ESI emitter, which in turn transmits the eluting sample to a MS or other detector. The line for introducing the mobile phase to the column is split at the head of the column, one portion continuing on to pass through the column to perform the analytical separation, and the second portion constituting a "waste stream" across which the voltage for ESI emission is applied, and which, by controlling the diameter of the exit from the waste stream, permits control over the flow speed of the mobile phase. By slowing down the mobile phase, the elution peak for any specific moiety may be broadened, permitting thorough characterization of the same by the detector.

Described below is a method for performing a similar experiment using two different lengths of fused silica capillary as restrictors which control the column flow between fast (100→>200 nL/min) and slow (<10–30 nL/min) mobile phase flow rates using a common commercial HPLC syringe pump system. The mobile phase can be switched to low flow as a peptide begins to elute, broadening elution peaks sufficiently to allow $MS^n$ experiments to be performed on multiple analytes in a single HPLC run, even when the masses of the peptides are not known ahead of time.

In order to couple HPLC with a sheathless $\mu$-ESI source, a method must be provided to supply the $\mu$-ESI potential to the HPLC effluent. Currently, there are two methods for applying the potential needed for $\mu$-ESI to the $\mu$-ESI emitter tip: direct contact though metal emitters or metalized tips and liquid junctions.[3,6-9] Metal emitters suffer from background attributable to the metal, while metalized tips have limited lifetimes of often less than one day. Liquid junctions typically have issues with background ions due to the metal of the liquid junction or instability due to formation of bubbles in or past the junction. Here we present a novel liquid junction for coupling HPLC with $\mu$-ESI overcoming peak width limitations, chemical noise problems, and stability issues.

The apparatus includes a standard HPLC column which is provided with a split or "T" at the head of the column, between the column itself and the eluant reservoir/pump. The waste column is equipped with a metal contact, or applied charge across the column, for providing the potential for the ESI emitter at the end of the HPLC column. A MS is adjacent to the ESI capillary. By controlling the flow rate of the waste column, preferably with a multi-opening diverter, the flow rate can be controlled and HPLC peaks broadened to provide opportunities for repeated sampling, more MS experiments and therefor complete characterization of biological molecules of interest being eluted.

DETAILED DESCRIPTION OF THE DRAWINGS

In each of the above Figures, the HPLC system of FIG. 1 was used with the value in high flow (100–200 nL/min) position throughout the entire gradient. Elution peak widths are typically 15–25 seconds.

In each of the above Figures, the HPLC system was switched from high flow (100–200 nL/min) to low flow (10–30 nL/min) at 3.3 min (arrow Ss and then switched back to high flow at 6.1 min (arrow f).

These chromatograms clearly show the ability of the system to rapidly slow down the flow over the column resulting in a broadening of elution time.

These Figures demonstrate the ability to slow the flow and, thus, increase the elution times of multiple peaks. The arrows indicate times when the value position was switched from high flow (arrow s) or low flow to high flow (arrow f).

FIGS. 5A–5H illustrate the high sensitivity of the HPLC-$\mu$ FSI system. Horse heart Cytochrome C was digested with trypsin and the equivalent of 1.5 fmol of Cytochrome C was analyzed.

The selected ion chromatograms are shown for base peak and eight (8) tryptic fragments of Cytochrome C, with the corresponding residue numbers of each peptide being indicated.

The experiment was performed with the system in high flow (100–200nL/min) mode throughout the entire gradient. The peak widths of the peptides are typically 20 seconds.

The equivalent of 1.5 fmol of Cytochrome C was analyzed using the HPLC-$\xi$ESI system described. The system was run at high flow mode with a peptide of interest being observed in the MS spectrum. The flow was then rapidly switched to slow flow and CAD spectra were collected. Upon complete acquisition of CAD information, the flow was returned to high flow until the next peptide eluted.

Five CAD spectra were collected with ease without pre-programming or pre-selecting the peptide to be analyzed by CAD. All five CAD spectra indicated Cytochrome C as the parent protein when searched using MS-Tap.

This system has been used to collect thousands of CAD spectra in one run without pre-selection of the peptides to be analyzed.

This invention embraces an apparatus for controlling the flow rate of HPLC elution, and broadening the peaks thereof, so as to permit characterization of molecules, particularly biological ones, in the elution fraction, through ESI MS. By carefully controlling eluant flow, while controlling for dead volume, precise characterization of the molecules eluted may be obtained.

Figure 1:
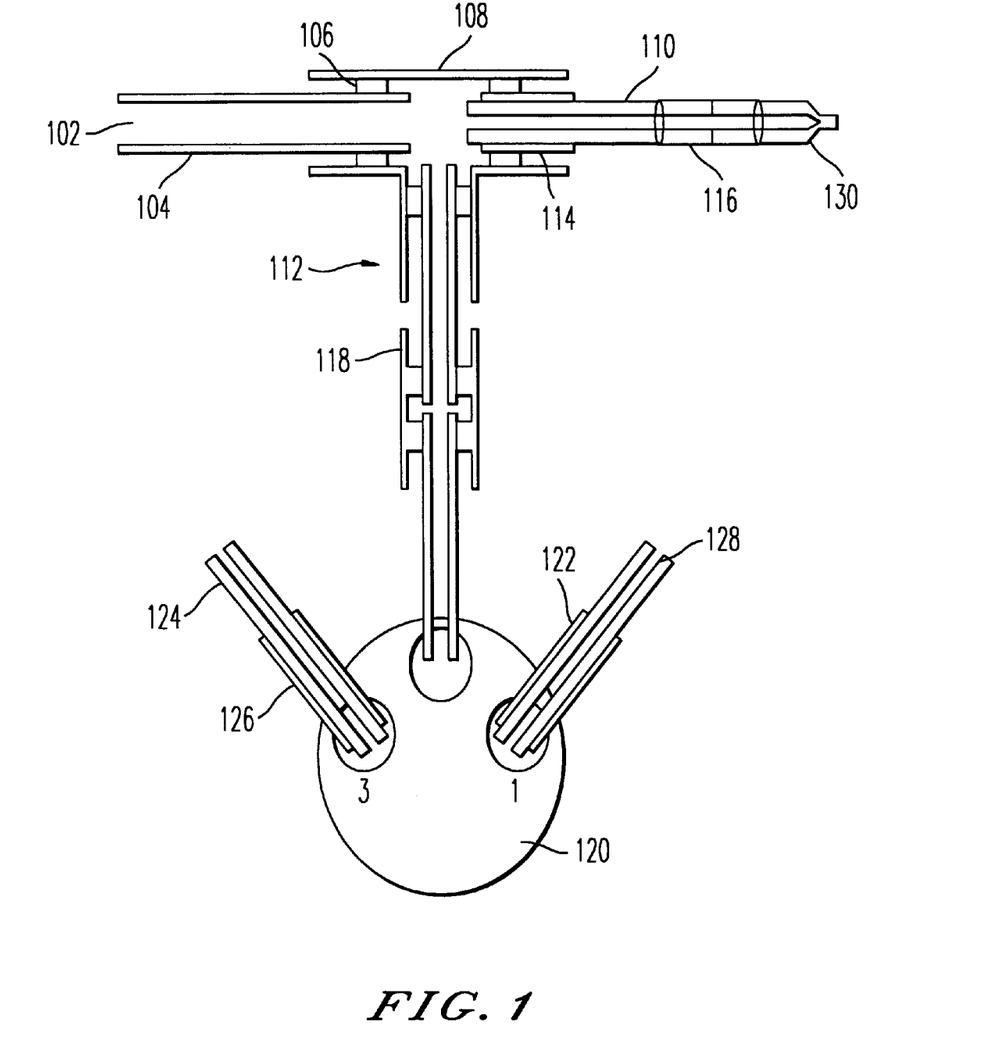
FIG. 1 illustrates an HPLC-$\mu$ESI system used for controlling the elution times of peptides from a reverse phase column. With the value in position 1–2, the mobile phase flow rate over the column is 100–200 nL/min., giving HPLC peak widths of 10–25 seconds. When the value is in position 1–3, the flow rate over the column is typically 10–30 nL/min., producing HPLC peak widths of 1.5–5 min.
Figure 2A:
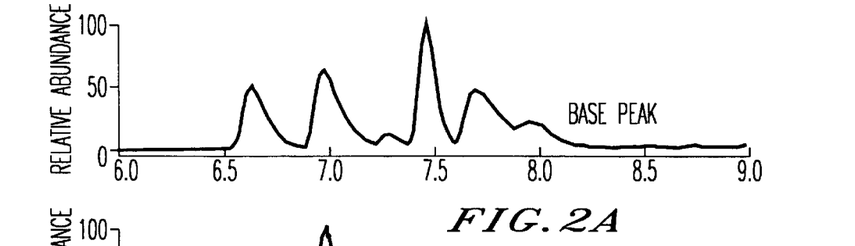
FIG. 2A illustrates a base peak ion chromatogram.
Figure 2B:
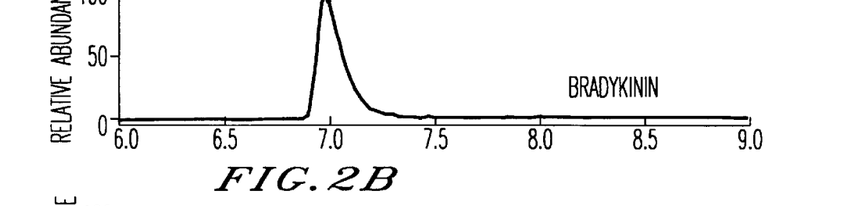
FIG. 2B illustrates an ion chromatogram for 100 fmol of Brodykinin.
Figure 2C:
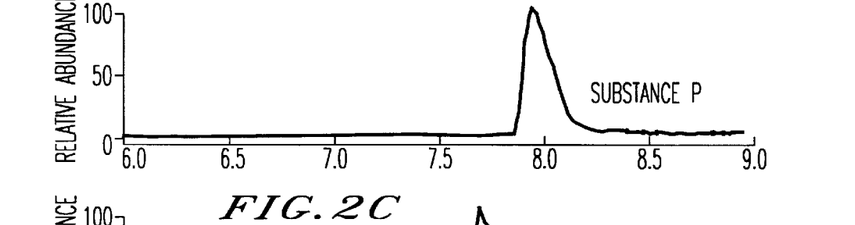
FIG. 2C illustrates an ion chromatogram for 100 fmol of Substance P.
Figure 2D:
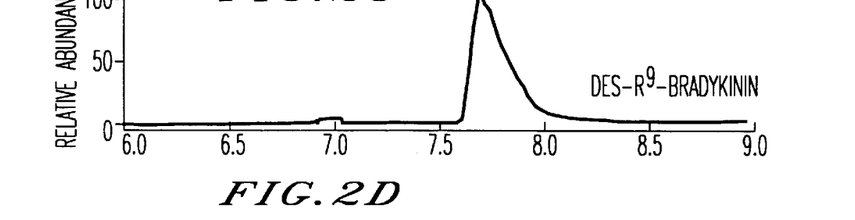
FIG. 2D illustrates an ion chromatogram for 100 fmol of Des-$R^9$-Bradykinin.
Figure 2E:
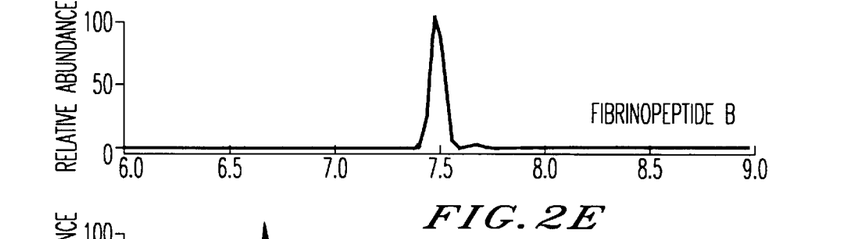
FIG. 2E illustrates an ion chromatogram for 100 fmol of Dynorphine A (1–13).
Figure 2F:
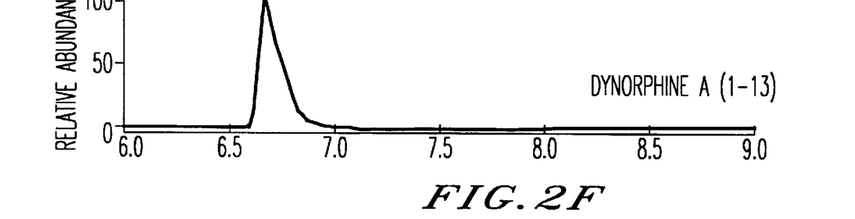
Figure 3A:
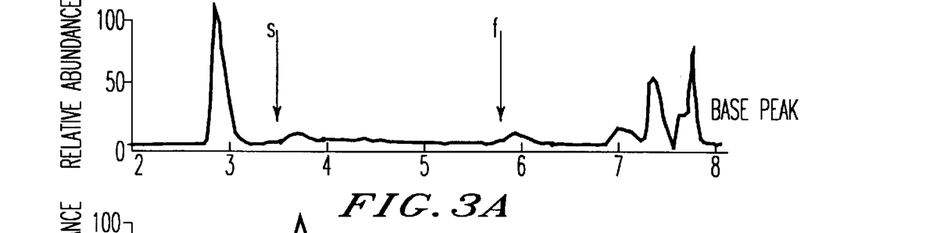
FIG. 3A illustrates a base peak ion chromatograph.
Figure 3B:
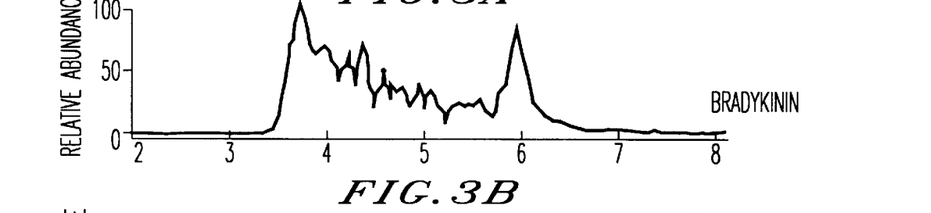
FIG. 3B illustrates an ion chromatograph for 100 fmol of Bradykinin.
Figures 3C, 3D:
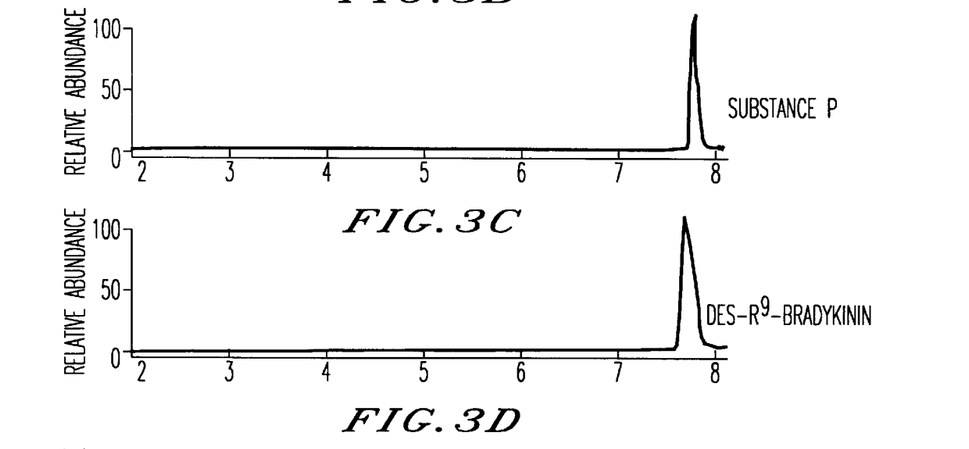
FIG. 3C illustrates an ion chromatograph for 100 fmol of Substance P.
FIG. 3D illustrates an ion chromatograph for 100 fmol of Des-$R^9$-Bradykinin.
Figures 3E, 3F:
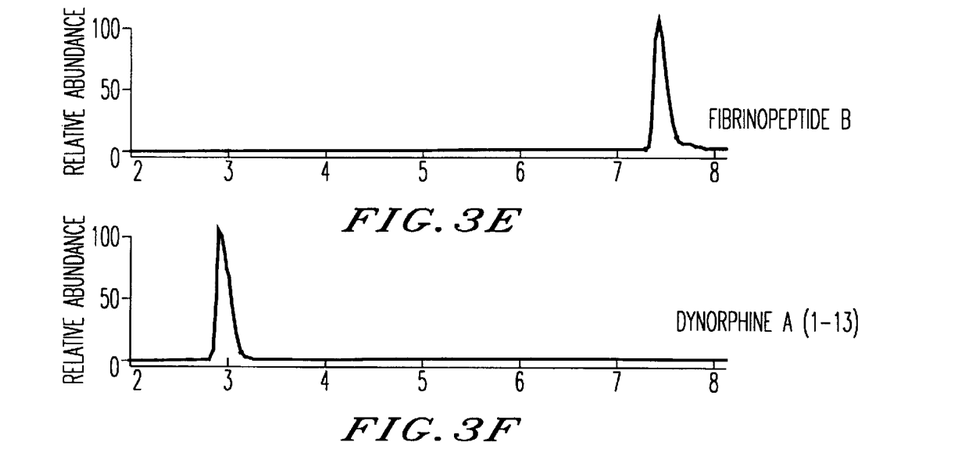
FIG. 3E illustrates an ion chromatograph for 100 fmol of Fibrinopeptide B.
FIG. 3F illustrates an ion chromatograph for 100 fmol of Dynorphine A (1-B).
Figure 4A:
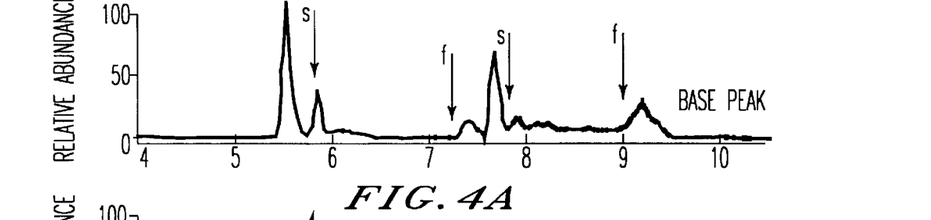
FIGS. 4A–4F illustrate, respectively, ion chromatograms of the same peptides as in FIG. 2.
Figure 4B:
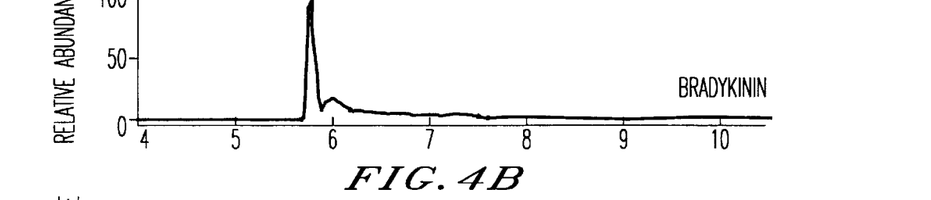
Figure 4C:
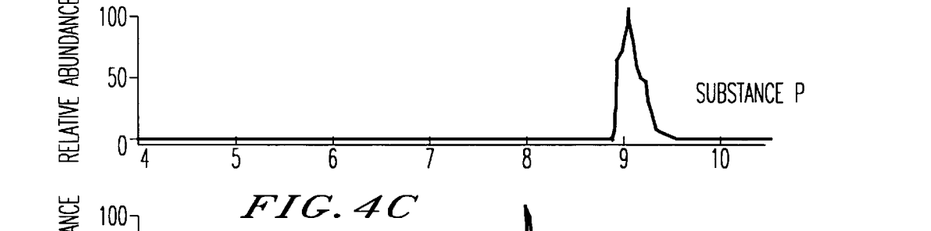
Figure 4D:
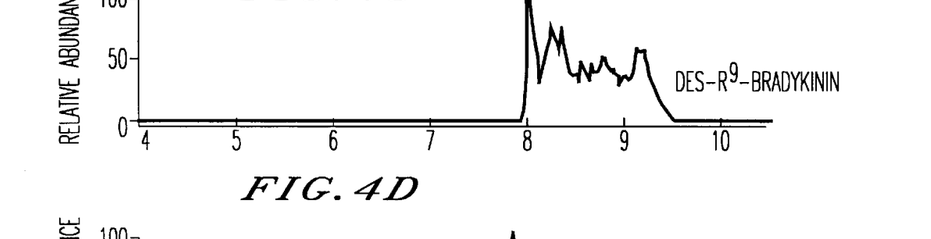
Figure 4E:
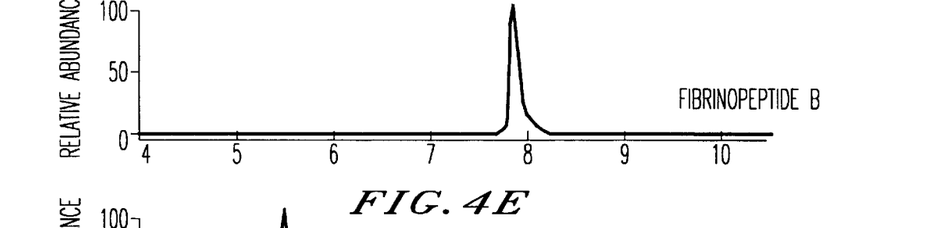
Figure 4F:
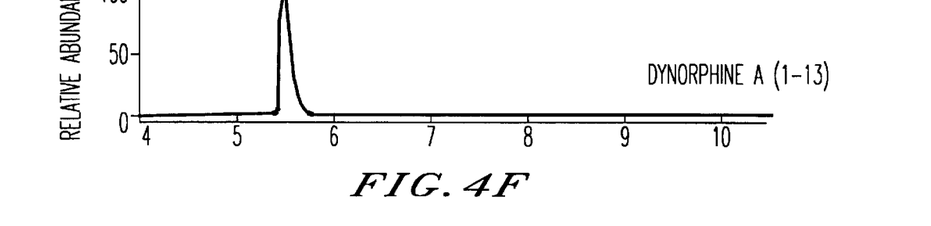
Figure 5A:
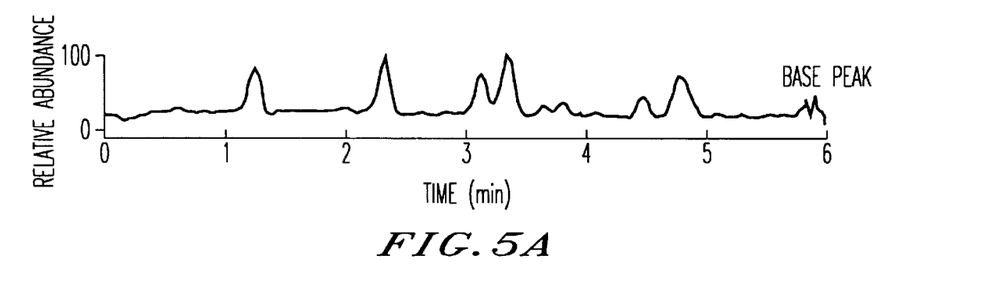
Figure 5B:
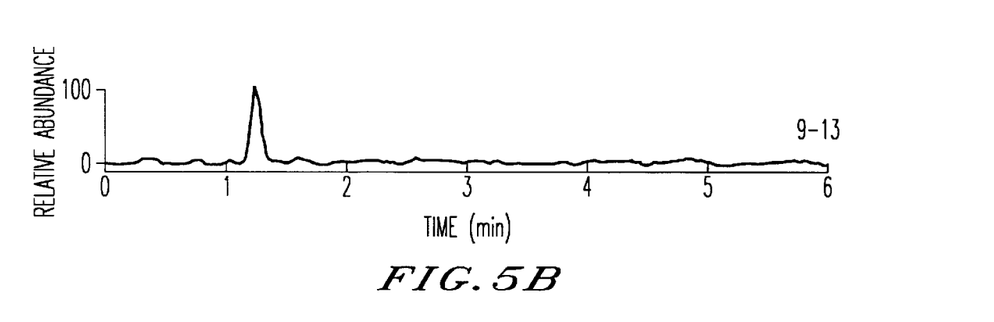
Figure 5C:
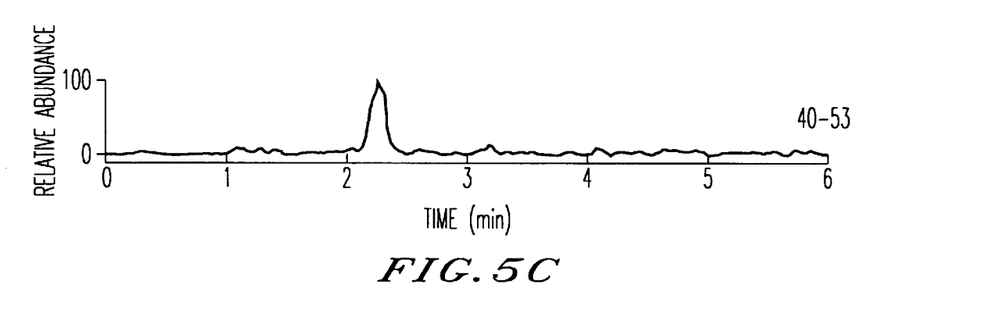
Figure 5D:
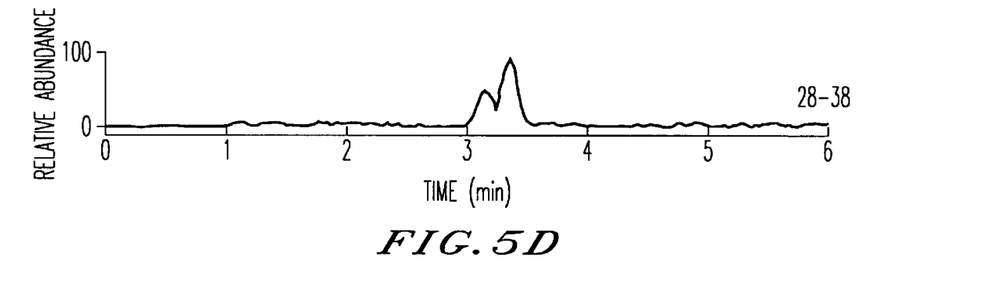
Figure 5E:
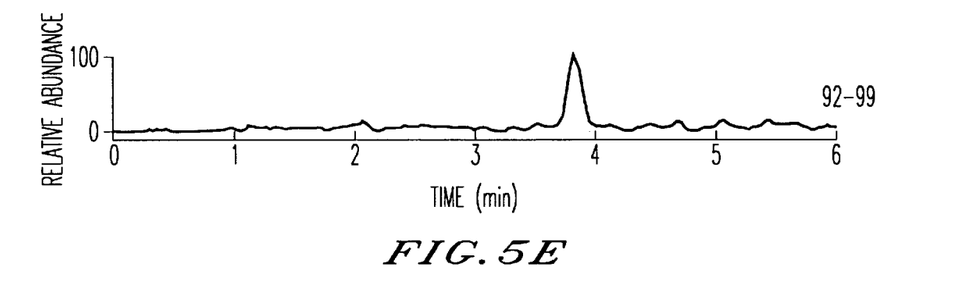
Figure 5F:
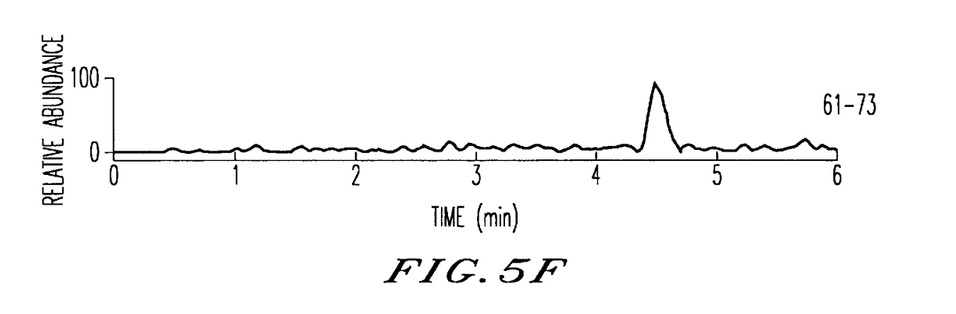
Figure 5G:
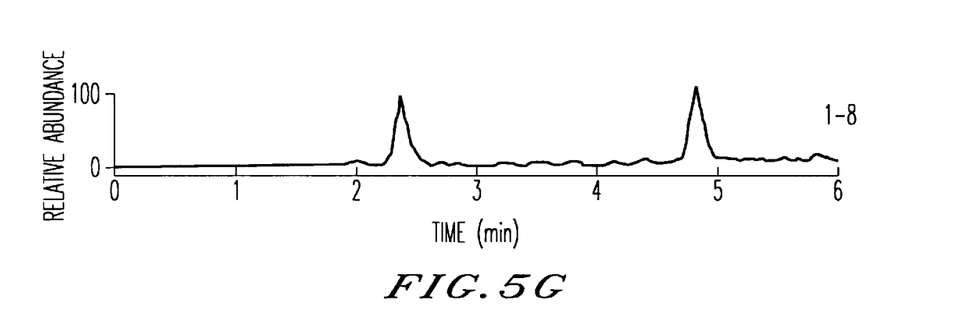
Figure 5H:
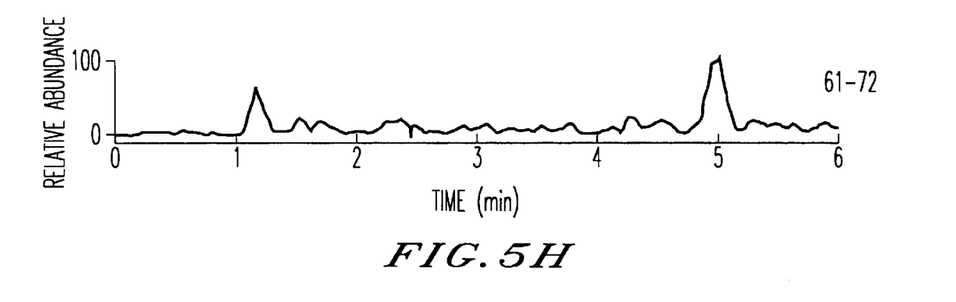

The apparatus is illustrated in FIG. 1. The mobile phase enters the apparatus 100 at a point upstream 102 from the actual HPLC column, coming from the mobile phase pumps (not pictured). This entry point is conventional polyetheretherketone (PEEK) tubing 104 or other suitable fluid conduit. This tubing is fitted into a fitting (PEEK ferule) 106 which holds the tubing in tight association with the HPLC column 110 through a "T" fitting 108 which splits the flow into two streams, one entering the column 110 and one referred to as the "waste" stream 112, which permits control over flow rate. The column itself comprises tubing 110 joined through a connector 116 to an ESI emitter 130 which may be an FSC or may be a metallic tip if the charge potential is not applied directly to the tip. In a preferred embodiment, voltage for the electric potential is applied to metal fittings or union 118 across the waste line or stream 112.

In a preferred embodiment, the apparatus of the invention is provided with a diverter 120, as shown in FIG. 1. In this embodiment, the diverter valve may occupy multiple positions corresponding to openings of different diameter 122 and 124 which give different flow rates, permitting differential broadening of HPLC peaks at different stages of the elution. In this embodiment, the diverter opening may comprise PEEK tubing 126 coupled with capillaries 128 of different volume.

The apparatus is used to perform HPLC—ESI mass spectrometry of peptides and other biological compounds, based on elution pattern. The mobile phase enters the waste stream and column head, the waste stream slowing column flow and controlling for "dead volume" in advance of actual passage through the HPLC column. By controlling the speed of flow in the waste stream, by varying the diameter of the exit opening therefore, the speed of passage of the mobile phase may be retarded, and therefore the "elution peak" broadened, to permit repeated sampling, fragmentation and characterization of the biological moiety in question. The invention may be further understood by reference to the Examples set forth below, which are not intended to be limiting.

Experimental

HPLC columns were prepared by packing 5 cm of a 7 cm×360 m.×75 m. fused silica capillary (F.C., Polymicro Technologies, Phoenix, Ariz.) with 10 m. C-18 beads YMC (Wilmington, N.C.) as reported previously.[9] HPLC gradients were formed using an ABI (foster city, Calif.) 140B syringe pump system. Gradients were 0–60% B (A=0.1 M $CH_3COOH$ in $H_2O$, B=$CH_3CN$) in 19 min. The 200 $\mu L$/min flow from the syringe pump was split at the head of the column using a Swagelock ZDV tee (Richmond, Va.) with the waste passing through a titanium ZDV union (Valco, Houston, Tex.) then into a Valco Six Port two position divert valve (Finnigan, San Jose, Calif.) as shown in FIG. 1. The divert valve regulated the column flow by allowing switching between two different FSC. restrictors located in the mobile phase waste line. The restrictors were chosen to give the desired column flow and peak broadening, and were typically 360 m.×50 m.×10 cm and 280 m.×100 m.×5 cm for the high and low flow rates respectively. Column flow rates were generally switchable between ca. >150 nL/min and <20 nL/min.

ESI emitters were prepared by hand pulling 360 m.×50 m. FSC using the method of Davis and Lee.[7] Briefly, a 400 g weight was suspended from the FSC. The FSC was then heated with a bright blue flame produced by a modified Microflame micronox torch (Mennetonka, Minn.). The torch was modified by replacing the flame tip with a 22 gauge stainless steel needle. The pulled FSC filaments were then cut to the desired o.d./i.d. under a microscope using a razor blade and butt connected to the end of the HPLC column using a piece of Teflon drilled to 368 m. i.d. as shown in FIG. 1.

ESI voltage was applied to the metal union in the split waste line utilizing the conductivity of the HPLC mobile phase to get the potential to the emitter tip. Typical voltages were 1.4–2 kV dc. The distance of the metal union to the tip of the $\mu$-ESI emitter was ca. 18 cm. The distance of the emitter to the heated capillary orifice was ca. 1 mm.

All analysis were performed on a LCQ (Finnigan MAT, San Jose, Calif.) ion trap mass spectrometer. Spectra were collected with automatic gain control (AGC) on, AGC targets of $2\times10^7$ and $7\times10^7$ for MS and Ms$^n$ scan modes respectively, and maximum injection times of 500 ms. AGC is used to control the number of ions that are stored in the trap to overcome space charge limitations. A scan on the LCQ consists of both an AGC prescan and an analytical microscan, each repeated n times (3 in our case) as specified by the user. The AGC prescan determines the ion flux in 3 ms and then calculates the injection period required to give the AGC target values requested by the user. All spectra were recorded in centroid mode using a mass range of 300–2000 m/z. Database searches were performed using the MS-Tag program http://rafael.ucsf.edu/) with the Swiss-Prot database.

The peptide standards (bradykinin, substance P, des-R$^9$-bradykinin, fibrinopeptide B, and dynorphin A(1–13), Sigma Chemical Co., St. Louis, Mo.) were made by adding the appropriate amount of peptide to 1% $CH_3COOH$, 5% $CH_3CN$ to give a final concentration of ca. 1 nmol/$\mu L$ in 1 mL. Each of these peptide standards were then diluted in 1 mL 1% $CH_3COOH$ to give a standard peptide mixture containing five peptides at a concentration of ca. 1 pmol/$\mu L$ each. 250 pmol of Horse Heart Cytochrome C from Sigma (St. Louis, Mo.), was digested overnight with Promega (Madison, Wis.) modified trypsin, in 40 $\mu l$ of ammonium acetate (pH=8.0) at a protein:enzyme ratio of 25:1. The Cytochrome C samples described below were dilutions of this digest.

Results and Discussion

FIGS. 2–4 show selected ion current chromatograms recorded for the separation of 5 standard peptides. FIG. 2 shows the separation and peak widths obtained without switching to low flow rate. FIG. 3 demonstrates the resultant peak broadening after reducing the flow and the subsequent narrowing of the peaks with a return to high flow rate. Peak widths before broadening were ca. 24 seconds. After reducing the flow, the peak width of the analyte peak was increased to ca. 3 minutes. The width of the peak after reducing the flow is dependant on the ratio of the flow before reduction to that of the flow after reduction. The stability of the low flow $\mu$-ESI is the only factor limiting the reduction in flow and therefor the peak width. For these experiments the pulled F.C. were used to increase the stability of low flow $\mu$-ESI operation. Stable $\mu$-ESI was easily achieved at flow rates of between 10 and 20 nL/min after reduction while maintaining stable high flow operation. FIG. 4 illustrates the ability to resume a HPLC run after a slow flow experiment and slow the flow for another later eluting analyte.

Figure 6A:
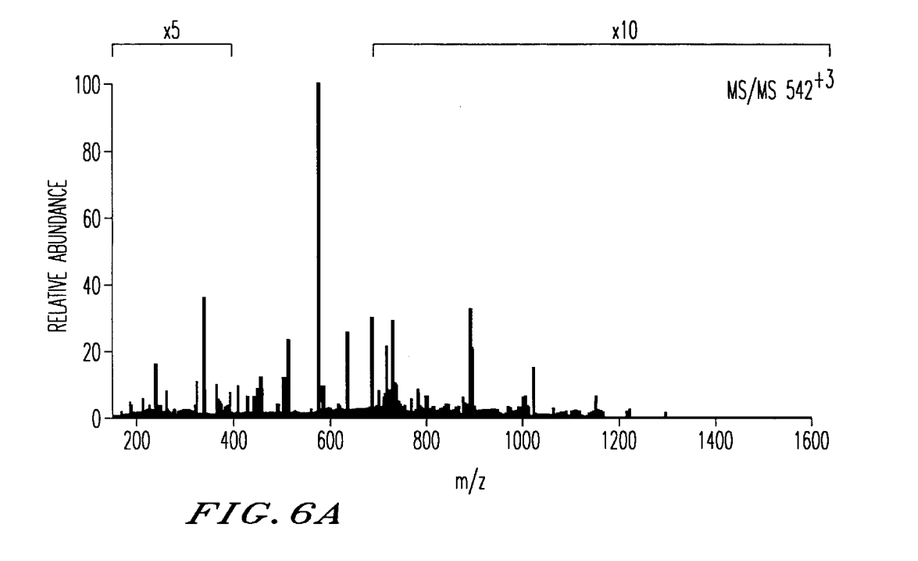
FIGS. 6A–6B illustrate CAD spectra for two tryptic fragments of Cytochrome C is indicated.
Figure 6B:
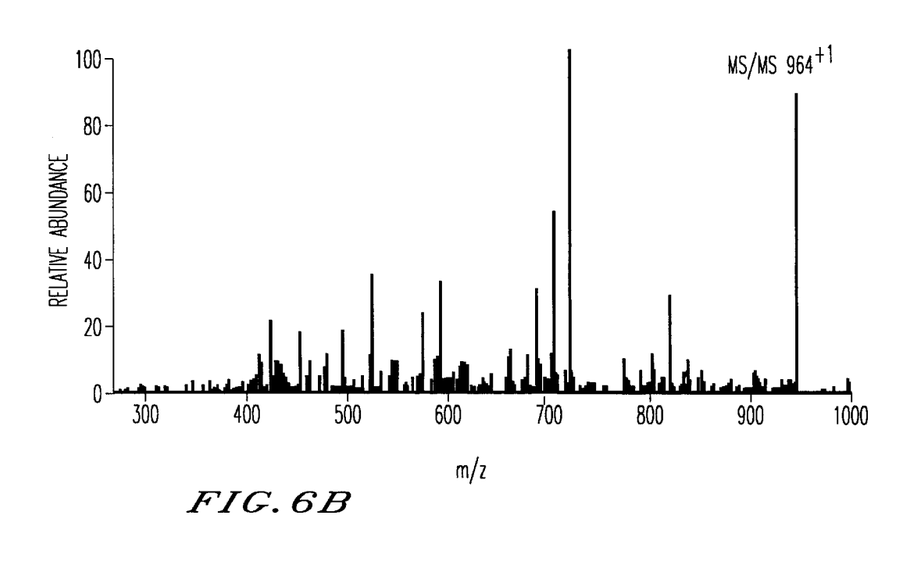

FIG. 5 shows the selected ion chromatograms for several peaks seen in a HPLC separation of a tryptic digest of Cytochrome C at the 1.5 fmol level. This illustrates the ability of the system to afford excellent separations at low sample levels. FIG. 6 shows two examples of the high quality MS/MS CAD spectra obtained using this system at these low sample levels. Five of the CAD mass spectra were input into the MS-Tag protein database search program. Each of these spectra gave Cytochrome C as the parent protein.

We have shown a system capable of rapid switching between HPLC flow rates. This system was inexpensive, easy to construct, required no modifications to current HPLC systems, and is fully controllable. The system provided stable electrospray, provided less background ions than other methods of $\mu$-ESI voltage application and did not adversely affect HPLC separations. Routine application of sheathless $\mu$-ESI coupled to MS detection will benefit from this setup.

This method of increasing peak widths can easily be applied to any detection technique (NMR, ESR, etc.) benefitting from longer analysis times for an eluting HPLC peak.

This invention has been described in generic terms, and by reference to specific embodiment. Specific embodiments, examples and experiments are not intended to be limiting, and variations will occur to those of skill in the art without the exercise of inventive faculty. Variations in composition, detector means, specific equipment and the like remain within the scope of the invention, unless excluded by the claims set forth below.

References

1. Biemann, K. *Annu. Rev. Biochem.* 1992, 61, 977–1010.
2. Cox, A. L.; Skipper, J.; Chen, Y.; Henderson, R. A.; Darrow, T. L.; Shabanowitz, J.; Englehard, V. H.; Hunt, D. F.; Slingluff, C. L. Jr. *Science* 1994, 264, 716–719.
3. Wahl, J. H.; Gale, D. C.; Smith, R. D. *J. Chromatogr. A* 1994, 659, 217–222.
4. Wilm, M. S.; Mann, M. *J. Mass Spectrom. Ion Processes* 1994, 136, 167–180.
5. Wilm, M. S.; Mann, M. *Anal. Chem.* 1996, 68, 1–8.
6. Kriger, M. S.; Cook, K. D.; Ramsey, R. S. *Anal. Chem.* 1995, 67, 385–389.
7. Davis, M. T.; Stahl, D. C.; Lee, T. D. *J. Am. Soc. Mass Spectrom.* 1995, 6, 571–577.
8. Davis, M. T.; Stahl, D. C.; Hefta, S. A.; Lee, T. D. *Anal. Chem.* 1995, 67, 4549–4556.
9. Hunt, D. F.; Alexander, J. E.; McCormack, A. L.; Martino, P. A.; Michel, H.; Shabanowitz, J.; Sherman, N.; Moseley, M. A.; Jorgenson, J. W.; Tomer, K. B. *Techniques in Protein Chemistry II;* J. J. Villafranca, Ed.; Academic Press, New York, 1991; pp. 441–454.

What is claimed is:

1. A method of characterizing a moiety from a sample, comprising:

(a) introducing a mobile phase gradient which elutes said moiety at some point in said gradient into a high performance liquid chomatograhy (HPLC) column in which said sample has been loaded, (b) directing said mobile phase through said column and thence to an apparatus for effecting electrospray ionization (ESI) in communication with a detector which characterizes said moiety when it elutes from said column, wherein the period of time over which said moiety is eluted is broadened by reducing a speed at which said mobile phase passes through said column and wherein said speed is reduced by splitting said mobile phase into two streams upstream of said column, directing one said stream through said column and directing the other said stream away from said column and through an opening which is of a diameter which slows the speed of flow of said mobile phase.

2. The method of claim 1, wherein said detector is a mass spectrophotometer, a nuclear magnetic resonance detector, or an electron spin resonance detector.

3. The method of claim 1, wherein said ESI comprises a fused silica capillary (FSC).

4. The method of claim 1, wherein said moiety is a biological moiety.

5. The method of claim 4, wherein said biological moiety is a peptide.

* * * * *

UNITED STATES PATENT AND TRADEMARK OFFICE
CERTIFICATE OF CORRECTION

PATENT NO. : 6,315,905 B1 Page 1 of 1
DATED : November 13, 2001
INVENTOR(S) : Robert E. Settlage et al.

It is certified that error appears in the above-identified patent and that said Letters Patent is hereby corrected as shown below:

<u>Column 1,</u>
Line 4, the following paragraph is inserted immediately after the title:
-- U.S. Government Rights
This invention was made with United States Government support under Grant No. GM37537, awarded by the National Insitutes of Health. The United States Government has certain rights in the invention. --

Signed and Sealed this

Eighteenth Day of June, 2002

*Attest:*

*Attesting Officer*

JAMES E. ROGAN
*Director of the United States Patent and Trademark Office*